US007045354B2

(12) United States Patent
McDonald et al.

(10) Patent No.: US 7,045,354 B2
(45) Date of Patent: May 16, 2006

(54) PROCESS FOR SCALED-UP PRODUCTION OF RECOMBINANT PROTEINS USING TRANSGENIC PLANT SUSPENSION CULTURES

(75) Inventors: Karen A. McDonald, Fairfield, CA (US); Alan P. Jackman, Davis, CA (US); Melody M. Trexler, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 486 days.

(21) Appl. No.: 09/992,845

(22) Filed: Nov. 14, 2001

(65) Prior Publication Data

US 2002/0120953 A1 Aug. 29, 2002

Related U.S. Application Data

(60) Provisional application No. 60/248,913, filed on Nov. 14, 2000.

(51) Int. Cl.
*C12N 5/14* (2006.01)
*C12N 15/15* (2006.01)
*C12N 15/82* (2006.01)

(52) U.S. Cl. ............ 435/419; 435/420; 435/431; 800/320.2

(58) Field of Classification Search ........ 800/278, 800/288, 298, 320.2; 536/23.1, 23.5, 24.1; 435/419, 420, 431
See application file for complete search history.

(56) References Cited

U.S. PATENT DOCUMENTS

| | | | |
|---|---|---|---|
| 4,064,015 A | 12/1977 | Nyiri et al. | |
| 5,407,816 A * | 4/1995 | Bringi et al. | ....... 435/123 |
| 5,693,506 A | 12/1997 | Rodriguez | |
| 6,127,145 A | 10/2000 | Sutliff et al. | |

FOREIGN PATENT DOCUMENTS

WO    WO 95/14099    5/1995

OTHER PUBLICATIONS

Des Molles, D.V. et al., "Expression of a Carrot Invertase Gene in Tobacco Suspension Cells Cultivated in Batch and Continuous Culture Conditions," *Journal Bioscience Bioeng.*, 87:302-306 (1999).
Fischer, U. et al., "Semicontinuous cultivation of photoautotrophic cell suspension cultures in a 20 l airlift-reactor," *Plant Cell, Tissue and Organ Culture*, 38:123-134 (1994).
Huang, N. et al., Metabolic regulation of α-amylase gene expression in transgenic cell cultures of rice (*Oryza sativa* L.), *Plant Molecular Biology*, 23:737-747 (1993).
Huang, N. et al., "Structural organization and differential expression of rice α-amylase genes," *Nucleic Acids Research*, 18(23):7007-7014 (1990).
Moorhouse, S.D. et al., "A plant cell bioreactor with medium-perfusion for control of somatic embryogenesis in liquid cell suspensions," *Plant Growth Regulation*, 20:53-56 (1996).
Ozturk, S.S., "Engineering challenges in high density cell culture systems," *Cytotechnology*, 22:3-16 (1996).
Phisalaphong, M. and Linden, J.C., "Kinetic Studies of Paclitaxel Production by *Taxus canadensis* Cultures in Batch and Semicontinuous with Total Cell Recycle," *Biotechnol. Prog.*, 15:1072-1077 (1999).
Ryland, J.R. et al., "Effect of Gelatin on the Stability of Heavy Chain Monoclonal Antibody Production from Plant Suspension Cultures," *J. Microbiol. Biotechnol.* 10(4):449-454 (2000).
Scragg, A.H. et al., "Growth of *Catharanthus roseus* suspensions for maximum biomass and alkaloid accumulation," *Enzyme Microb. Technol.*, 12:292-298 (1990).
Seki, M. et al., "Taxol (Paclitaxe) Production Using Free and Immobilized Cells of Taxus cuspidata," *Biotechnology and Bioengineering.*, 53(2):214-219 (1997).
Su, W.W. and Lei, F., "Perfusion Strategy for Rosmarinic Acid Production by *Anchusa officinalis*," *Biotechnology and Bioengineering*, 42(7):884-890 (1993).
Su, W.W. et al. "High density cultivation of *Anchusa officinalis* in a stirred-tank bioreactor with in situ filtration," *Appl. Microbiol, Biotechnol.*, 44:293-299 (1995).
Su, W.W. et al., "A perfusion air-lift bioreactor for high density plant cell cultivation and secreted protein production," *Journal of Biotechnology*, 50:225-233 (1996).
Ten Hoopen, H.J.G. et al., "Continuous Culture of Suspended Plant Cells," *In Vitro Cell Dev. Biol.*, 28P: 115-120 (1992).
Terashima, M. et al., "Effects of sugar concentration on recombinant human $\alpha_1$-antitrypsin production by genetically engineered rice cell," *Biochemical Engineering Journal*, 6:201-205 (2000).
Terashima, M. et al., "Production of functional human $\alpha_1$-antitrypsin by plant cell culture," *Appl. Microbiol. Biotechnol.*, 52:516-523 (1999).
van Lier et al., "Long-term semi-continuous production of recombinant baculovirus protein in a repeated (fed-) batch two-stage reactor system", Enzyme and Microbial Technology 18:460-466 (1996).
Glick et al., "Molecular Biotechnology: Principles and Applications of Recombinant DNA", ASM Press, Washington, D.C., p. 312, lines 1-8, (1994).

* cited by examiner

*Primary Examiner*—Russell P. Kallis
(74) *Attorney, Agent, or Firm*—Townsend and Townsend and Crew LLP (57) ABSTRACT

The present invention relates to methods for semi-continuous culture of plant cells in a nutrient medium. The pH of the medium is monitored during the cell culture as a way of monitoring the expression of a product of interest by the cells.

5 Claims, 3 Drawing Sheets

PROCESS FOR SCALED-UP PRODUCTION OF RECOMBINANT PROTEINS USING TRANSGENIC PLANT SUSPENSION CULTURES

CROSS-REFERENCES TO RELATED APPLICATIONS

The present application claims priority to U.S. Ser. No. 60/248,913, filed Nov. 14, 2000, herein incorporated by reference.

BACKGROUND OF THE INVENTION

Plant cell culture is currently being studied as an alternative to using transgenic plants, microorganisms, yeast cells, or insect and mammalian cell cultures for recombinant protein production (Magnuson et al., Protein Expres. Purif. 13, 45–52 (1998); Fischer et al., Biotechnol. Appl. Biochem. 30, 109–112 (1999); Doran, P. M., Curr. Opin. Biotech. 11, 199–204 (2000); James et al., Protein Expres. Purif. 19, 131–138 (2000)). Some advantages of using plant cell suspension cultures for production of biologically active compounds are low raw material costs, capability of post-translational modifications, and diminished risk of mammalian pathogen contamination.

One of the major drawbacks of plant cell culture production systems is the slow growth rate of plant cells. Traditional batch cultures include a long lag time to allow growth of plant cells to productive levels. After maximal cell growth occurs, the cells are harvested with the product and the process begins again.

Studies using the constitutive CaMV 35S promoter in transgenic tobacco have observed improved results with semi-continuous and continuous systems versus batch systems for production of extracellular foreign proteins (Des Molles et al., J. Biosci. Bioeng. 87, 302–306 (1999); Ryland et al., J. Microbial. Biotech. 10, 449–454 (2000)). Intermittent medium exchanges have also been implemented using wildtype plant cultures where secondary metabolite production was elicited (Scragg et al., Enzyme Microb. Tech. 12, 292–298 (1990); Su et al., Biotechnol. Bioeng. 42, 884–890 (1993); Su et al., Appl. Microbiol. Biot. 44, 293–299 (1995)). Since these secondary metabolites were not secreted, they could only be harvested once a maximum concentration was reached intracellularly. Therefore, the effects of revitalizing and reusing the plant cells for subsequent growth and expression phases could not be evaluated. However, recent research has demonstrated higher yields of secreted taxol in wildtype plant cultures using re-elicitation and periodic medium renewal compared to single batch type cultures (Phisalaphong et al., Biotechnol. Prog. 15, 1072–107 (1999); Wang et al., Appl. Microbiol. Biot. 55, 404–410 (2001)).

Inducible promoters allow regulated gene expression, and therefore independent control and optimization of the growth and product expression phases. Traditional batch culture is not well suited to the use of inducible promoters because of the lag time and expense of restarting the culture with each harvest. A continuous culture is also undesirable for an inducibly regulated promoter since it would be difficult to implement rapid changes in the concentration of regulatory molecules.

There has been little research involving maximizing productivity in plant cell cultures by applying the benefits of an inducible promoter to the long term, semi-continuous production of a secreted recombinant protein. This type of operation can help make plant cell culture economically attractive for recombinant protein production compared to other hosts or transgenic plants, depending on production level and downstream processing costs.

Previous work demonstrated production of a human therapeutic protein, recombinant $\alpha_1$-antitrypsin (rAAT), in transgenic rice (Oryza sativa L.) suspension cultures (U.S. Pat. No. 6,127,145). Use of an inducible rice $\alpha$-amylase (RAmy3D) promoter to direct expression of a heterologous protein and use of a rice $\alpha$-amylase signal peptide to direct secretion of a heterologous protein into the culture medium have been disclosed. (Huang N. et al., Plant Mole. Biol. 23, 737–747 (1993); Rodriguez, WO 95/14099.) The RAmy3D promoter and signal peptide were originally disclosed in Huang N., et al., Nucl. Acids Res. 18, 7007–7014 (1990). Production of rAAT in transgenic rice cultures has also been demonstrated by Terashima and coworkers (Terashima et al., Appl. Microbiol. Biot. 52, 516–523 (1999); Terashima et al., Biochem. Eng. J. 6, 201–205 (2000); Terashima et al., Biotechnol. Prog. 17, 403–406 (2001)).

Maximization of protein productivity from plant tissue culture cells would be assisted by semi-continuous operation combined with identification of optimal conditions for cell growth and protein expression. Semi-continuous large scale growth of plant cells occurs over a long time period, thereby increasing the risk of contamination of the culture. Currently, optimal conditions for growth and expression of protein are identified by techniques that require sampling of the culture and time-consuming off-line analysis, such as viable cells counts and immunological identification of protein products. Sampling of the culture is undesirable due to the potential to introduce microbial contaminants from the surrounding environment as the sample is taken. Contamination would render the batch unusable. In addition, the optimal time for performing medium exchanges could be missed due to the length of time required for off-line analysis. Identification of easily assayable variables or on line measurements that correlate with vigorous cell growth or high levels of protein expression would increase the effectiveness of this method of protein production. The present application addresses these and other needs.

BRIEF SUMMARY OF THE INVENTION

The present invention relates to a method for semi-continuous culture of plant cells in a nutrient medium. The pH of the medium is monitored during the cell culture as a way of monitoring the expression of a protein product of interest by the cells.

In one embodiment, the plant cells contain a heterologous expression cassette with a polynucleotide encoding the expressed protein product under the control of a promoter. In another embodiment, the promoter is an inducible promoter. A promoter from an $\alpha$-amylase gene can be used. In a particular aspect, the $\alpha$-amylase promoter is from the RAmy3D.

In one embodiment, the polynucleotide encoding the expression product is a human $\alpha_1$-antitrypsin polynucleotide. In another embodiment, the human $\alpha_1$-antitrypsin gene is optimized for expression in plant cells.

In one aspect, the medium exchange occurs when the pH is above 5.5. In a another aspect, the medium exchange occurs when the pH is above 6.5.

In another embodiment, cells are cultured in an induction medium to induce expression of the product of interest from an inducible promoter. Medium exchange is then carried out with a growth medium to enhance growth and viability of the cells.

In another embodiment, the plant cell is a rice cell.

In one embodiment, the oxygen uptake rate of the plant cells is measured. In another embodiment, a growth medium is exchanged with an induction medium when the oxygen uptake rate is above 2.0 mmol $O_2$/L hour. In a further embodiment, a growth medium is exchanged with an induction medium when the oxygen uptake rate is above 5.0 mmol $O_2$/L hour.

The present invention relates to a method for production of a recombinant expression product using semi-continuous culture of transgenic plant cells. The transgenic plant cells contain a heterologous expression cassette with a polynucleotide encoding the expression product of interest under the control of an inducible promoter. Induction medium is exchanged with a growth medium when the pH of the medium is above 5.0.

In one aspect, the transgenic plant cells are rice cells. In another aspect, the expression product is encoded by a human $\alpha_1$-antitrypsin polynucleotide.

In one embodiment, the oxygen uptake rate of the plant cells is measured. Growth medium is exchanged with the induction medium when the oxygen uptake rate is above 2.0 mmol $O_2$/L hour.

BRIEF DESCRIPTION OF THE DRAWINGS

FIG. 1. Metabolic activity and viability during the growth and expression phases. Cell viability was measured using Evan's blue dye and a hemocytometer to count viable cells. Oxygen uptake rate (OUR) was determined by first measuring the levels of dissolved oxygen in the medium, and then calculating the rate of consumption of oxygen.

DETAILED DESCRIPTION OF THE INVENTION

I. Introduction

The present invention is based on observations made during semi-continuous culture of rice cells to produce recombinant human α-1-antitrypsin (rAAT) under the control of an inducible promoter. The promoter, RAmy 3D, is activated during growth in sugar free media and cells were cultured in a medium with sucrose to promote growth, followed by growth in a medium without nutritive sugar in order to induce production of protein. After production of protein, sugar free medium containing the protein product was removed and exchanged for medium with sugar to restart cell growth. This cycle can be continued indefinitely.

As explained below, when cells produce heterologous protein, the pH of the media rises as expressed protein levels increase. pH measurement is thus conveniently used as an indicator of protein production and as an indicator of when the heterologous protein can be harvested or when media can most optimally be exchanged back to growth medium if an induction medium is used. In those embodiments in which have starting pH values of about 5.0, increased protein production can be associated with pH levels above 5.0, usually above 5.5, typically above 6.0, preferably above 6.5, more preferably above 7.0, and occasionally above 7.5. Typically the upper pH limit for medium exchange will be less than pH 8.5, preferably less than pH 8.0.

One of skill in the art will recognize that the pH value for optimal protein production will vary with the culture conditions, the type of cells, and the protein produced. For example, pH levels will rise after the switch to sugar free induction medium and then level off. The increase and leveling off of pH levels will depend on many variables, including those listed above.

The present invention also provides improved methods for determining cell viability. As shown below, during the growth phase in medium containing sugar, cell cultures have increased viability levels when rates of oxygen uptake are at their highest levels. High cell viability can indicate a preferred time to induce protein production. Increased cell viability can be associated with oxygen uptake rates above 1.0 mmol $O_2$/(L hour), usually above 1.2 mmol $O_2$/(L hour), preferably above 1.4 mmol $O_2$/(L hour), more preferably above 1.6 mmol $O_2$/(L hour), most preferably above 1.8 mmol $O_2$/(L hour), and frequently above 2.0 mmol $O_2$/(L hour).

II. Defintions

The term "plant cell" includes cells derived from any part of a plant, including shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), or plant tissue (e.g. vascular tissue, ground tissue, and the like) or particular cells (e.g. guard cells, egg cells, trichomes and the like), and progeny of same. The class of plant cells that can be used in the method of the invention is generally as broad as the class of higher and lower plants amenable to cell culturing techniques, including angiosperms (monocotyledonous and dicotyledonous plants), gymnosperms, ferns, and multicellular algae. It includes plant cells of a variety of ploidy levels, including aneuploid, polyploid, diploid, haploid and hemizygous plants.

The term "semi-continuous culture" refers to growth of cells in culture medium in a culture vessel, followed by removal of all or some of the medium while the cells are retained in the culture vessel. Fresh medium is then added to the cells. The fresh medium may have the same components or different components than the original unspent medium. For example, "induction medium" may be exchanged with "growth medium," or the reverse may also occur.

The term "induction medium" refers to medium which provides a culture environment that activates transcription or alleviates repression of transcription from an inducible promoter.

The term "growth medium" refers to medium which allows growth and division of plant cells. Growth medium, generally speaking, is not optimal for production of protein from an inducible promoter.

The term "expression product" refers to a protein or other compound of interest that is expressed from plant cells during cell culture. The protein may be expressed from a heterologous expression cassette or, alternatively, may be expressed from a naturally occurring gene in the plant cell chromosome.

The term "heterologous expression cassette" refers to a polynucleotide sequence that has been engineered to be expressed in cell of interest. For instance, a heterologous expression cassette comprising a promoter operably linked to a second polynucleotide may include a promoter that is heterologous to the second polynucleotide as the result of human manipulation of an isolated nucleic acid comprising the expression cassette. (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)). In another example, a heterologous expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide sequence is "heterologous" to a cell or a second polynucleotide sequence if it originates from a foreign species, or, if from the same species, is modified from its original form. For example, a promoter operably linked to a heterologous coding sequence refers to a coding sequence derived from a species different than that from which the promoter was derived, or, if from the same species, a coding sequence which is not naturally associated with the promoter (e.g. a genetically engineered coding sequence or an allele from a different ecotype or variety).

"Polynucleotide" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52): 35095–35101 (1998).

The term "promoter" refers to regions or sequence located upstream and/or downstream from the start of transcription and which are involved in recognition and binding of RNA polymerase and other proteins to initiate transcription.

The term "inducible promoter" refers to a promoter that is regulated in response to an environmental condition. Environmental conditions include, for example presence or absence of metabolites, such as nutritive sugars or amino acids; presence or absence of small molecules, including hormones or antibiotics; and temperature of the growth media.

III. Growth of Plant Tissue Culture Cells

Methods of growing plant tissue culture cells are known to those of skill in the art. For semi-continuous culture, cells are cultured in medium that is exchanged after a period of time for fresh medium. Cells are not removed from the culture vessel during the medium exchange.

A. Equipment and Media for Growth of Plant Tissue Culture Cells.

Plant tissue culture cells can be grown on a small scale or on a large scale. Scaled-up culture of plant cells generally refers to cultures of five or more liters of cells. Cells are grown under sterile conditions with agitation and controlled $O_2$ levels. Agitation can be provided by a low shear impeller. The temperature can also be controlled to enhance the growth of cells or to enhance expression of proteins. Those of skill in the art will appreciate that optimal growth conditions will be different for tissue culture cells derived from different plant species and will know to adjust culture conditions accordingly.

The composition of media for growth of plant tissue culture cells is known to those of skill in the art. Media for the purposes of this invention may be altered to include or exclude components, depending on the type of promoter used. The pH of the medium is preferably not controlled.

Measurement of pH is well known to those of skill in the art. pH can be measured using a pH electrode in combination with a device for reporting the pH. pH can also be detected using pH sensitive dyes, usually bound to a paper support. pH electrodes, pH meters, and pH paper are all commercially available from, for example, Fisher Scientific, Inc., and Broadley-James Corporation.

One of skill in the art would know how to measure dissolved oxygen levels in media, and how to use those levels to determine a rate of oxygen consumption over time. Dissolved oxygen sensors are commercially available from, for example, Broadley-James Corporation and Mettler Toledo Corporation.

The bioreactor or culture vessel will preferably include means to measure dissolved $O_2$ levels and the pH of the medium. Measurements can be taken online, within the bioreactor vessel or measurements can be taken offline, after samples of the medium have been withdrawn from the vessel, however, online measurements are preferred.

Samples can be taken from the bioreactor vessel during the culture of plant cells, as long as precautions are taken to maintain the sterility of the culture. Those of skill in the art are familiar with techniques to maintain sterility. Aseptic techniques include using a sterile tube welder to make connections between the bioreactor vessel and sampling syringe and/or product harvest vessel using flexible tubing. Alternatively, samples can be taken directly from the bioreactor vessel by opening the bioreactor in a laminar flow hood.

Media is exchanged from the bioreactor vessel for a variety of reasons, including to induce protein production, to harvest the protein of interest, or to restart growth of the cells after nutrient depletion. One of skill in the art will understand that media exchange can be carried out in a variety of ways. Sterile media can be added by filtration through a sterile filter. Media can be removed from the bioreactor vessel by using a peristaltic pump to draw media through a sterile tube welder from the bioreactor into flexible tubing, for example.

During semi-continuous culture, cells are retained in the bioreactor while the media is removed. Methods for cell retention include gravity sedimentation, centrifugation, spin filters, and membrane systems. When designing a medium exchange device for plant cell suspensions, long term (2–3 months) operation with repeated cycles is considered. Since plant cells typically grow as aggregates, rather than single cells, and have relatively low metabolic rates compared with microbial or mammalian cells, gravity sedimentation is a useful option for cell retention. Gravity sedimentation is a simple and reliable cell retention technique that minimizes contamination potential because it can be performed entirely within the bioreactor. When agitation and aeration cease, a clarified zone propagates from the liquid surface downward as the cell aggregates settle, leaving a "clarified" liquid phase on top of a "settled-cell" phase. This clarified liquid phase can then be drawn off and replaced with a different medium.

B. Measurement of Cell Growth and Metabolism During Growth of Plant Tissue Culture Cells.

One of skill in the art will know that tissue culture cells can be derived from many different plants. The invention thus has use over a broad range of types of plants, including species from the genera *Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Zea, Avena, Hordeum, Secale, Triticum,* and *Sorghum*.

For example, plants cells derived from monocots may be used, particularly the members of the taxonomic family known as the Gramineae. This family includes all members of the grass family of which the edible varieties are known as cereals. The cereals include a wide variety of species such as wheat (*Triticum* sps.), rice (*Oryza* sps.) barley (*Hordeum* sps.) oats, (*Avena* sps.) rye (*Secale* sps.), corn (*Zea* sps.) and millet (*Pennisettum* sps.). In the present invention, preferred family members are rice and barley.

Plant tissue culture cells may also be derived from dicots, including tobacco, tomato, and potato plants.

1. Measurement of Cell Growth.

Those of skill in the art know that growth of cells can be determined in many different ways. For example, plant cell growth in culture can be determined by measuring the fractional settled cell volume (FSCV), the fractional packed cell volume (FPCV), or the biomass concentration. FSCV is determined by removing a sample of cells from the bioreactor vessel, allowing the cells to settle in a container for about ten minutes, and recording the volume of the settled cell phase. Alternatively, the FSCV can be measured directly in the bioreactor once agitation and aeration are turned off and the cells are given time to settle through gravitational forces, if the interface between the clarified liquid and the settled cell phase can be visualized or measured. FPCV is measured by removing a sample of cells from the bioreactor vessel, centrifuging the cells, and recording the volume of packed cells.

Biomass concentration is the grams of dry weight of cells per liter of culture. Dry weight of cells is determined by placing a sample containing cells from the bioreactor vessel onto pre-weighed filter paper, removing media by suction, washing the cells with water, drying the cells, and weighing them.

In addition to use of oxygen uptake measurements, one of skill can use a variety of methods to determine cell viability. For example, viability of the cells in culture can be determined by dye exclusion assays. Those of skill in the art know to count viable cells in culture using an appropriate dye and a hemocytometer. The technique is described in detail in *Current Protocols in Molecular Biology* Appendix A.3F.8. (Ausubel et al., eds., 1994)).

2. Measurement of Metabolites.

One of skill in the art would knows that the presence or absence of metabolites in the medium can be an indication of the health of cells in culture. In addition, if an inducible promoter is used, presence or absence of metabolites may indicate medium conditions that favor induction of transcription from the promoter. Metabolites that may be measured include sugars, nitrogen, and other molecules that induce transcription from a promoter or are indicative of the health of cells in culture.

3. Measurement of Oxygen Usage.

The rate of oxygen usage in tissue culture cells can indicate the metabolic state of cells in culture. Rapid utilization of oxygen can indicate cells are growing robustly and undergoing respiration. Oxygen usage can be measured by monitoring the disappearance of dissolved oxygen from the culture media as explained in more detail below.

IV. Expression of Proteins from Plant Tissue Culture Cells

The present invention is useful for production of many different proteins. Since cells are retained in the culture vessel during semi-continuous culture, the expressed protein is preferably secreted into the medium. Expressed proteins may be native to the plant cell and encoded by genes endogenous to the plant cell. Alternatively, proteins may be expressed from transgenic plant cells that carry a heterologous expression cassette including a gene that encodes a protein of interest. Proteins expressed from heterologous expression cassettes may be engineered to include a signal peptide for secretion, if the protein is not normally secreted.

A. Methods to Construct a Heterologous Expression Cassette.

Methods to make vectors that express proteins using the present invention are known to those of skill in the art. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

An exemplary vector for use in the present invention will comprise a chimeric gene (or expression cassette) designed for expression in plants, with companion sequences upstream and downstream from the expression cassette. Upstream companion sequences include promoter sequences and DNA sequence that encode amino acid sequences that direct secretion of a protein of interest (signal sequences). Downstream sequences include termination sequences to promote efficient translation of mRNA.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

The plant promoter may direct expression of the gene of interest under more precise environmental control. Such promoters are referred to here as "inducible" promoters. Examples of environmental conditions that may effect transcription by inducible promoters include anaerobic conditions, nutrient availability, elevated temperature, or the presence of light. Examples of inducible promoters include those that transcribe the cereal α-amylase genes and sucrose synthase genes, and are repressed or induced by small molecules, like sugars, sugar depletion or phytohormones such as gibberellic acid or absissic acid. Representative promoters include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes. These promoters are described, for example, in ADVANCES IN PLANT BIOTECHNOLOGY Ryu, D. D. Y., et al, Eds., Elsevier, Amsterdam, 1994, p. 37, and references cited therein; Other suitable vectors include the sucrose synthase and sucrose-6-phosphate-synthetase (SPS) promoters from rice and barley.

A number of chemically inducible promoters are known to function in plants. For a review, see Zuo and Chua, *Curr. Op. Biotech.* 11, 146–151 (2000). Promoters regulated by alcohol are known. (Caddick et al., *Nature Biotechnol.* 16, 177–180 (1998); Salter et al. *Plant J.* 16, 127–132 (1998)). As are promoters regulated by presence or absence of glucocorticoid (Aoyama and Chua, *Plant J.* 11, 605–612 (1997)), tetracycline (Gatz et al., *Plant J.* 2, 397–404 (1992)), pristinamycin (Frey et al., *Biotech. Bioengr.* 74, 154–163 (2001)), and copper (Mett et al., *Proc. Natl. Acad. Sci. USA* 90, 4567–4571 (1993)).

In addition, promoters regulated by nutrient concentration (e.g. phosphate and carbohydrate) have been identified. For example, rice α-amylase promoters, such as the RAmy3D and αAmy8 promoters, have been shown to be rapidly and strongly induced under sugar deprivation conditions in rice plants (Thomas et al. 1994. Gene regulation and protein secretion from plant cell cultures: the rice alpha-amylase system, in Advances in Plant Biotechnology, Ryu, D D et al., eds. Elsevier, New York, pp 37–55; Simmons and Rodriguez 1989. High level synthesis and secretion of alpha-amylase from rice callus, in Biocatalysis in Agriculture Biotechnology, Whitaker, J. R. Ed., American Chemical Society, Washington, D.C., pp 203–214) and in rice cell suspension cultures (Yu et al., *J. Biol. Chem.* 266, 21131–21137 (1991); Yu et al., *Gene* 122, 247–253 (1992); Huang et al., *Plant Mole. Biol.* 23, 737–747 (1993)). Chan et al. demonstrated that the αAmy8 promoter also functions in transgenic tobacco cell cultures, and that induction or suppression of αAmy8 protein expression could be readily reversed by the manipulation of sugar level in the medium. (Chan et al., *J. Biol. Chem.* 269, 17635–17641 (1994)).

In addition to a promoter sequence, the expression cassette can also contain a transcription termination region downstream of the structural gene to provide for efficient termination. The termination region can be obtained from the same gene as the promoter sequence or may be obtained from different genes.

In addition to encoding the protein of interest, the expression cassette can encode a signal peptide that allows processing and translocation of the protein, as appropriate. Suitable signal sequences are described in above-referenced PCT application WO 95/14099. Preferred signal sequences are derived from the RAmy3D promoter. A plant signal sequence is placed in frame with a heterologous nucleic acid encoding a peptide or protein such that signal peptidase cleavage occurs precisely at the start of the mature peptide.

To enhance the production of heterologous proteins in plant cells, the DNA sequence which encodes the heterologous protein may be modified to include predominantly the most used codons of the plant cell host. Codon usage tables for plant species are known to those of skill in the art, and are available at http://www.kazusa.or.jp/codon/. Care should be taken to ensure the amino acid sequence of the protein is not changed.

Other features of vectors useful in the present invention are known to those of skill in the art. The vector will typically include a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta. Other elements that are typically included in expression vectors include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences.

An exemplary construct for expression of heterologous proteins under the control of an inducible promoter is described in Huang et al., herein incorporated by reference. (Huang et al., *Biotechnol. Prog.* 17, 126–133 (2001)). The construct includes the rice RAmy3D promoter, the RAmy3D first intron and signal peptide, as well as the RAmy3D terminator.

B. Transformation of Plant Cells with a Heterologous Expression Cassette.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

V. Characterization and Purification of Expressed Proteins

A. Characterization of Proteins Produced Using Semi-continuous Plant Cell Tissue Culture.

The particular protein produced using semi-continuous plant cell tissue culture the present invention is not critical to the invention. Many types of proteins can be produced using the present invention, including without limitation, therapeutic proteins, antibodies, enzymes, protease inhibitors, transport proteins, storage proteins, protein toxins, hormones, and structural proteins.

Methods are available to ensure that the protein of interest is being made by correctly by the plant tissue culture cells. Immunological detection can conveniently be used to detect the protein of interest. In addition, depending on the expressed protein, functional assays can be designed to detect the presence of active protein. If appropriate, assays may also be done to determine whether the protein of interest is post-translationally modified.

1. Immunological Detection of Proteins.

If an appropriate antibody is available, immunoassays can be used to qualitatively or quantitatively analyze the proteins produced using the present invention. A general overview of the applicable technology can be found in Harlow & Lane, *Antibodies: A Laboratory Manual* (1988).

The proteins of the interest can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7$^{th}$ ed. 1991). Immunological binding assays (or immunoassays) typically use an antibody that specifically binds to a protein or antigen of choice. The antibody may be produced by any of a number of means well known to those of skill in the art and as described in Harlow & Lane, *Antibodies: A Laboratory Manual* (1988).

Western blot (immunoblot) analysis may be used to detect and quantify the presence of the protein of interest in the sample. Western blot analysis can further be used to ensure a full length protein has been produced. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the protein of interest. The antibodies may be directly labeled or alternatively may be subsequently detected using labeled secondary antibodies (e.g., labeled sheep anti-mouse antibodies) that specifically bind to the primary antibodies.

2. Functional Assays of Proteins.

Many different proteins can be expressed using the present invention; thus, many different assays for functional protein may be employed. One of skill in the art will be aware of the particular assay most appropriate to determine the functional activity of the expressed protein.

3. Post-translational Modification of Expressed Proteins.

Post-translational modification of expressed proteins can also be determined by one of skill in the art. There is great diversity in the post-translational modification of proteins. (Reviewed in *Methods in Enzymology: Posttranslational Modifications*, volumes 106 and 107 (Wold and Moldave, eds.)) Analysis of glycosylation of the expressed protein may be of particular interest to one of skill in the art. (For reviews see Kornfeld and Kornfeld *Annu. Rev. Biochem.* 54:631 (1985); Lis and Sharon, *Annu. Rev. Biochem.* 55:35 (1986); Kukuruzinska et al. *Annu. Rev. Biochem.* 56:915 (1987))

B. Standard Protein Separation Techniques for Purifying Proteins

Expressed proteins can be purified after production in a plant tissue culture system. The protein of interest may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when a protein of interest is being purified. For example, proteins having established molecular adhesion properties can be reversibly fused to the protein of interest. With the appropriate ligand, the protein can be selectively adsorbed to a purification column and then freed from the column in a relatively pure form. The fused protein is then removed by enzymatic activity. Finally, the protein of interest could be purified using immunoaffinity columns.

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of a protein of interest can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be purified using column chromatography as described below.

3. Column Chromatography

A protein of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

VI. EXAMPLES

The following examples are provided by way of illustration only and not by way of limitation. Those of skill in the art will readily recognize a variety of noncritical parameters that could be changed or modified to yield essentially similar results.

A. Growth of Rice Cells in a Bioreactor Under Semicontinuous Conditions.

Transgenic rice cell suspension cultures were viable for more than thirty days when grown in a bioreactor. The cells survived growth in media without a nutritive sugar source and resumed growth when returned to media containing sucrose.

1. Plant Cell Line and Media

Transgenic rice suspension cultures (Line 73-25) were provided by Applied Phytologics, Inc. (Sacramento, Calif., USA). A Japonica rice variety, TP309, was microprojectile bombarded with a vector, pAPI73, containing an rAAT gene that was codon optimized for expression in rice, with one amino acid substitution (Met358 to Val358) as described previously (Huang et al., *Biotechnol. Prog.* 17, 126–133 (2001)). The expression vector provided the rice α-amylase (RAmy3D) promoter, first intron and signal peptide, and terminator sequences.

Briefly, the expression vector described by Huang et al. was prepared starting with the Ramy3D gene sequence as described in Huang et al. *Plant Mol. Biol.*, 23:737–747 (1993). A 1.5 Kb Sal I fragment containing the promoter and part of the coding region was prepared from a genomic clone having the sequence shown in GenBank accession M59351 (Huang et al. *Nuc. Acids. Res.* 18:7007–7014 (1990). An Alu I fragment of that fragment containing 876 basepairs of promoter and 66 basepairs of 5' transcribed, untranslated region was then prepared and used as the promoter in the expression vectors of the invention. In addition, the first intron disclosed in GenBank accession M59351 was inserted into the 5' untranslated region of the expression cassette. The coding region of the codon optimized AAT gene was then inserted into the vector at a Not I/XhoI site. The codon optimized AAT sequence without the Met358 to Val358 substitution is described in U.S. Pat. No. 6,127,145.

Transgenic rice cell cultures were subcultured weekly by inoculating fresh AA medium (Thompson et al., *Plant Sci.* 47, 123–133 (1986)) containing 30 grams/liter of sucrose, denoted AA(+), at 32% density (volume of inoculating suspension to final volume of culture) using one-fifth of the shake flask volume. Flasks were kept at 26° C. and placed on an orbital shaker at 150 revolutions per minute under fluorescent light.

2. Bioreactor Operation

Large-scale transgenic rice cell cultures were grown in a New Brunswick Scientific BioFlo 3000 bioreactor (5-liter working volume) with a single pitched blade, low-shear impeller. Four and one half liters of AA(+) medium was sterile filtered into the bioreactor using a stainless steel pressure reservoir (Amicon), a 0.22-μm filter (Gelman Micro Culture Capsule), and compressed nitrogen at 5 psig. Shake flask cultures were combined to inoculate the bioreactor at a 10% density, based on the volume of inoculating suspension to final volume of culture.

Bioreactor conditions were maintained at 27° C., with an agitation speed of 75 rpm, and saturation of 70% based on dissolved oxygen measurement using an $O_2$ sensor from Mettler Toledo. During the last two expression phases, the dissolved oxygen setpoint was reduced to 40% air saturation. The dissolved oxygen level in the culture was controlled by manipulating the oxygen concentration in the gas sparging stream. The aeration rate was one liter/min, but sparging was performed intermittently between 0.17 min/min and 1.0 min/min. Oxygen uptake rate was monitored periodically by measuring the change in dissolved oxygen in the liquid in the absence of aeration.

The pH of the culture medium was monitored continuously online (Broadley James pH electrode) and periodically off-line (Fisher Scientific pH meter), however the medium pH was not controlled. Because both on-line pH and off-line pH measurements were consistent; only the on-line pH measurements are reported. The cultures grew under continuous ambient light conditions. Bioreactor conditions for the growth phases and the protein expression phases were identical, except for the dissolved oxygen setpoint as described above.

A sterile tube welder (Terumo SCD IIB) was used to make sterile connections of flexible tubing to the bioreactor vessel. For the first five days of the run, two to three samples each were taken using two different sampling methods: pipeting a sample through a port in the headplate after the bioreactor was transferred to a laminar flow hood or using a syringe in conjunction with the sterile tube welder. Since the tube welder method gave results that were consistent with the pipeting method and also minimized the potential for contamination, the tube welder was used in all subsequent sampling.

3. Cyclical Operation

Six medium exchanges were performed, encompassing three inductions of protein expression and three additions of growth medium for a total of three growth/production cycles. For the three inductions, AA medium without sucrose but containing 8 grams per liter of mannitol, denoted AA(−), was added in place of AA(+) growth medium. Mannitol was added in order to maintain the cell osmotic pressure and minimize cell disruption (Terashima et al., *Biochem. Eng. J.* 4, 31–36. (1999)).

The medium exchanges were performed by first connecting sterile tubing from an autoclaved ten liter carboy to the bioreactor using the sterile tube welder. A peristaltic pump was used to draw liquid from the bioreactor into the carboy. The medium was added by sterile filtration as described previously.

To remove the medium while retaining the cells in the bioreactor, medium exchanges 1–4 used a cylindrical gas diffusion stone/sparger with a pore retention size of 20 μm positioned at the bottom of the reactor and attached to the sample tubing. During the medium exchange the agitation and aeration were turned off. Medium exchanges 5 and 6 employed gravity sedimentation for removal of spent medium. The aeration and agitation were turned off; the cells allowed to settle for fifteen minutes; and then liquid was drawn off from the clarified phase through the sample port.

4. Biomass Measurements

Samples were collected and placed in fifteen milliliter graduated conical centrifuge tubes. Samples were allowed to settle for about ten minutes and the fractional settled cell volumes (FSCV) were recorded. The sample tubes were then centrifuged at 6500×g for ten minutes at 4° C., and the fractional packed cell volumes (FPCV) were determined. The supernatant in each tube was withdrawn with a syringe, filtered through a 0.22 µm filter into microfuge tubes, and frozen at −80° C. for later analysis of rAAT activity, total protein, and sugar concentration.

To obtain dry weight values, ten to fourteen milliliters of suspension sample were placed onto a pre-dried, pre-weighed, 0.22 µm filter connected to a vacuum. After medium removal, cells were washed with about thirty milliliters of distilled, deionized water. The cells were dried for four to five days at 60° C. For the viability staining, thirty microliters of a 1% Evan's Blue solution was added to 150 microliters of cell suspension. After ten minutes, 10 microliters of the stained solution was placed on a hemocytometer (Hausser Scientific) microscope slide, and the ratio of live to dead cells was determined.

5. Sugar Analysis

Extracellular sucrose, glucose, fructose, and mannitol concentrations were analyzed using a Hewlett Packard 1050 series HPLC system with a robotic automatic sampler, a Bio-Rad Aminex Resin Based Column (HPX-87C; 240×4 mm), and a Bio-Rad Carbo-C guard column. The column was equilibrated with filtered, degassed distilled, deionized water (the mobile phase), and then a ten microliter sample was injected into the column. The temperature of both columns was 85° C., the flow rate was 0.06 milliliters per minute, and each run sequence lasted 68 minutes. The sugars were detected by a Hewlett Packard 1047A Refractive Index (RI) detector set at 50° C. The RI detector was connected to a Hewlett Packard 35900C Multichannel Interface; data was processed by Hewlett Packard ChemStation software.

6. Medium Exchanges for Growth and Expression

The rice culture bioreactor run lasted for about thirty days, undergoing three growth phases with AA(+) sucrose medium and three expression phases with AA(−) mannitol medium. Medium exchanges provided conditions favorable for rice culture growth/rejuvenation and rAAT expression. During the first five days, the rice cells were cultured in AA(+) medium, and at day 5.1, the spent growth medium was removed with the gas diffusion stone and replaced with AA(−) induction medium (medium exchange 1, ME1). Cells were cultured in the induction medium until day 7.7 when the first induction broth containing rAAT was harvested and replaced with fresh AA(+) growth medium (ME2).

Following the second growth phase, on day 11.9, the spent growth medium was removed and replaced with AA(−) medium (ME3). This medium was harvested on day 16.9 and replaced with fresh AA(+) medium (ME4). However, during ME4, it became difficult to draw up liquid through the diffusion stone due to clogging, so only a partial medium exchange was performed (only half of the medium was removed and replaced with the same volume of fresh medium). Subsequent medium exchanges (ME5 and ME6) employed gravity sedimentation. Spent growth medium was exchanged for AA(−) medium on day 21.9 (ME5), and this medium, containing product, was finally harvested (ME6) on day 27.7.

A peristaltic pump was used to draw the mostly cell-free liquid from the bioreactor into a carboy at a flow rate of around 55 milliliter per minute for ME1, however the flow rate decreased with each subsequent medium exchange, reaching only approximately fifteen milliliters per minute for ME4. The flow rate for removal of the clarified liquid phases during ME5 and ME6 was manually adjusted to reach up to 235 milliliters per minute.

With the exception of ME3 and ME6, the working volume following the medium exchange was within 5% of the volume prior to the exchange. ME3 and ME6 resulted in 26% and 37% increases in volume, respectively, resulting in a more dilute cell suspension following the medium exchange. For ME1, the culture volume was 4.2 liters initially, 3.8 liters of spent medium was removed, and then 4.0 liters of AA(−) medium was added. Subsequent medium exchanges were as follows: ME2 (4.1 liters initially, 3.9 liters removed, 4.1 liters added), ME3 (3.9 liters initially, 3.0 liters removed, 4.0 liters added), partial ME4 (4.3 liters initially, 1.8 liters removed, 2.0 liters added), sedimentation ME5 (4.1 liters initially, 2.6 liters removed, 2.5 liters added), and sedimentation ME6 (3.5 liters initially, 2.1 liters removed, 3.4 liters added).

7. Effect of Cyclical Process on Cell Growth, Viability, and Respiratory Activity The initial biomass concentration ($x_0$), determined from a sample taken immediately after inoculation, was 0.4±0.1 gram of dry weight/liter with a 95% viability determined from Evan's Blue staining. The biomass concentration increased with successive growth phases and reached maximums of 4.1, 6.7, and 7.9 gram of dry weight/liter during the three cycles, respectively (Table 1). The maximum biomass concentration for cycle 1 was observed 1.2 days after the culture was induced, while the maximum biomass concentrations for both cycles 2 and 3 were observed during the growth phases, shortly before induction. The fractional packed cell volume was lower than the fractional settled cell volume, as anticipated. The FSCV and FPCV also increased significantly during the run, and maximums were observed during the third expression phase: FSCV was 0.38 and FPCV was 0.25.

TABLE 1

| | | | Growth Kinetic Data | | | | |
|---|---|---|---|---|---|---|---|
| Cycle | $t_{growth}$ (days) | $X_0$ (g dw/L) | max x (g dw/L) | $\mu_{max}$ (day$^{-1}$) | $\tau_D$ (days) | max OUR (mmol $O_2$/(L hr)) | max OURs (mmol $O_2$/(g dw hr)) |
| 1 | 5.1 | 0.4 | 4.1 | 0.47 | 1.5 | 2.8* | 0.84 |
| 2 | 4.0 | 2.6 | 6.7 | 0.26 | 2.6 | 5.6 | 0.90 |
| 3 | 4.8 | 4.4 | 7.9 | 0.19 | 3.7 | 2.0 | 0.29 |

*observed during the first expression phase

Logarithmic growth curves during the bioreactor run were analyzed. There were negligible lag phases for the first and second growth periods and a slight lag phase (about 2 days) for the third growth period. The maximum specific growth rates ($\mu_{max}$) decreased for each consecutive cycle, 0.47 day$^{-1}$ (doubling time or $\tau_d$=~1.5 days), 0.26 day$^{-1}$ ($\tau_d$=~2.6 days), and 0.19 day$^{-1}$ ($\tau_d$=~3.7 days), respectively.

Extracellular sucrose, glucose, fructose, and mannitol concentrations were determined during the cyclical process. Sucrose was hydrolyzed to glucose and fructose for all three growth phases, but a significant decrease in the two monosaccharide concentrations was observed only during the third growth phase. For growth phases 1 and 2, a medium exchange to AA(-) medium was performed before complete conversion of sucrose, and monosaccharide formation rate exceeded consumption rate during both of these phases. The sucrose concentration in the medium went from 28 to 14 grams per liter in five days for growth phase 1 and from 29 to 3 grams per liter in four days for growth phase 2. The glucose and fructose concentrations in the medium were similar for growth phases 1 and 2, reaching maximums of about 3.6–4.6 grams per liter. There was a sudden rise and subsequent decline in the sucrose concentration around days 4–5 during growth phase 1 and days 10–10.5 during growth phase 2, possibly due to the release of sucrose back into the medium.

The partial medium exchange (ME4), conducted on day 17, initiated the third growth phase with 15 grams per liter of sucrose instead of 30 grams per liter. Maximum glucose and fructose concentrations were observed (4.8 and 5.7 grams per liter, respectively) once sucrose became exhausted, and then the monosaccharides were non-preferentially consumed until the third induction was initiated (ME5). Since the cells were not drained dry using the sedimentation method, the starting sucrose concentration for growth phase 4 was only about 20 grams per liter.

For induction of protein expression using the transgenic rice cultures, a single medium exchange to AA(-) medium was completed (without washing the cells), and the concentrations of all three sugars were less than 1 gram per liter immediately after the medium exchange. During the three expression phases, the mannitol concentration stayed fairly constant around 6–8 grams per liter.

Figure 1:
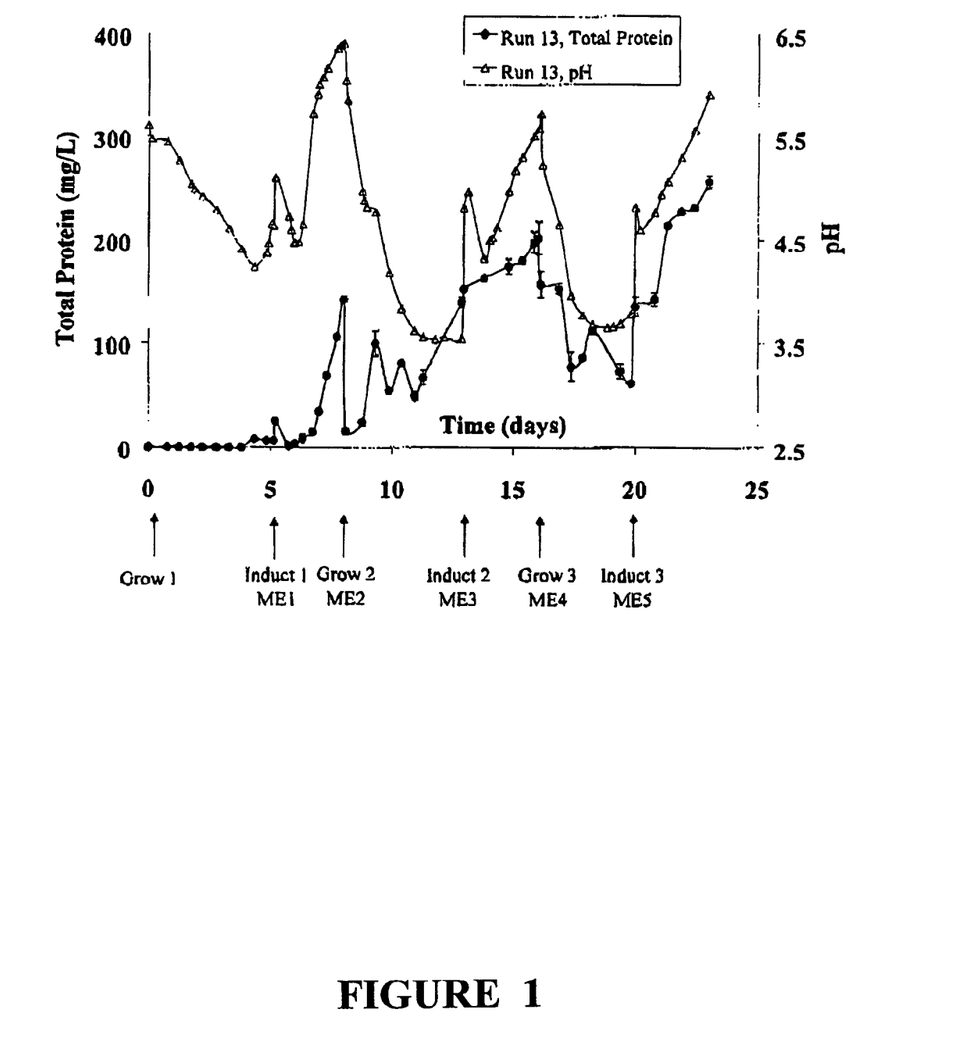

The oxygen uptake rate (OUR) and cell viability during the cyclical operation are shown in FIG. 1. Assuming that the solubility of oxygen in the culture medium at 27° C. is the same as the solubility of oxygen in pure water in equilibrium with air at 25° C. (0.25 mmol/liter), the maximum oxygen uptake rates observed during each of the three cycles were 2.8, 5.6, and 2.0 mmol O$_2$/(liter hr), respectively (Table 1). Maximum specific oxygen uptake rates of 0.84, 0.90, and 0.29 mmol O$_2$/(gram of dry weight per hour) were observed during each of the three growth phases, respectively.

During the second growth phase and the beginning of the second expression phase, the oxygen demand was so high that the control system was unable to maintain the dissolved oxygen level at 70%, even at a continuous sparging rate of 1.5 liters per minute of pure oxygen. In order to achieve steady state control, the dissolved oxygen setpoint was decreased to 40% one day into the second expression phase. A setpoint of 70% was used during the third growth phase, but the setpoint was again reduced to 40% during the third expression phase.

After the first and second induction medium exchanges (ME1 and ME3), cell biomass growth, oxygen uptake, and high viability continued for about 0.5–1.1 days. The highest OUR for cycle 1, was actually observed half a day into the first expression phase while for the other two cycles, the maximum OUR occurred during the growth phases. However, after this half day lag period that followed the induction medium exchange, the cell viability and OUR declined rapidly, presumably due to a lack of a carbon nutrient source.

Table 2 lists viable biomass concentrations and oxygen uptake rates at the beginning of each expression phase. For the first expression phase, the viability decreased from 78% to 40% within two days after induction, for the second expression phase, it decreased from 80% to 20% within five days, and for the third expression phase, it decreased from 55% to 20% within five days. Although the cell viability declined considerably during the extended expression phases, within one day after AA(+) medium was added to start growth phases 2 and 3, the biomass concentration, oxygen uptake rate, and cell viability had started to rise and the sucrose concentration began to drop.

TABLE 2

Culture Conditions at the Start of the Expression Phase

| Cycle | $x_v$ (g dw/L) | Cell Viability % | OUR (mmol O$_2$/(L hr)) | OURs (mmol O$_2$/(g dw hr)) |
|---|---|---|---|---|
| 1 | 2.3 | 78 | 2.8 | 0.41 |
| 2 | 4.2 | 80 | 2.6 | 0.42 |
| 3 | 3.7 | 55 | 1.8 | 0.23 |

B. Production of rAAT from Transgenic Rice Cell Suspension Cultures

1. Functional AAT Measurement

Porcine pancreatic elastase (PPE, Calbiochem), a serine protease that is inhibited by AAT, was used to determine the activity of rAAT produce from transgenic rice cell cultures. Reactions were carried out in 96-well microtiter plates. One hundred microliters of assay buffer (20 mM Tris, 150 mM NaCl, 0.01% Tween-80, pH 8.1), fifty microliters of either AAT standard (Human AAT, Calbiochem) or diluted rAAT samples from transgenic rice cell cultures, and 50 microliters of a PPE solution (10 µg/ml in assay buffer) were added to individual wells of a 96-well microtiter plate. Plates were then incubated at 37° C. for fifteen minutes. N-succinyl-Ala-Ala-Ala-p-nitroanilide (Sigma) is a chromogenic substrate of PPE. A 20 mM stock solution of N-succinyl-Ala-Ala-Ala-p-nitroanilide in DMSO was diluted to 4 mM in assay buffer, and then 50 microliters of this solution was added to each well. The initial reaction rate was obtained by monitoring the increase in absorbance at 405 nm using a microplate reader in the kinetic mode (Molecular Devices, SOFTmax software). Human AAT (Calbiochem) standard was used to develop a calibration curve relating authentic AAT concentration and residual PPE activity for analysis of functional rAAT (Huang et al., *Biotechnol. Prog.* 17, 126–133 (2001)).

2. Total Protein Measurement

Total extracellular protein concentration was measured using a Bradford assay (Bio-Rad). Reactions were carried out in triplicate in 96-well microtiter plates. Two to three separate assays were performed for the majority of the samples. Bovine serum albumin (BSA, Bio-Rad) was used as the protein standard.

3. SDS-PAGE and Immunoblotting

SDS-polyacrylamide gel electrophoresis (SDS-PAGE) was performed using 10% Tris-Glycine gels (BioWhittaker) in a Mini-Protean II (Bio-Rad) unit. Standards and samples were diluted with 5×SDS-PAGE loading dye, boiled for five minutes, and then ten microliters were loaded per well. The protein bands were stained with SimplyBlue SafeStain (Invitrogen). Human AAT (Calbiochem) was used as a standard.

For immunoblots, proteins were transferred from an SDS-PAGE gel to a nitrocellulose membrane using a Mini Trans-Blot unit (Bio-Rad). The primary antibody was rabbit anti-human AAT (DAKO); the secondary antibody was goat-anti rabbit IgG (H+L)-alkaline phosphatase conjugate (Southern Biotechnology). Immunoreactive AAT bands were detected by a colorimetric method using the BCIP/NBT substrate system (Bio-Rad). The immunoblot procedure has been described elsewhere (Huang et al., Biotechnol. Prog. 17, 126–133 (2001)).

4. Semi-Continuous Production of rAAT

Sustained production of functional rAAT was observed over three cycles. Maximum extracellular concentrations of rAAT reached 40 milligrams per liter (2.5 days after induction; 7.7 day total cycle time), 110 milligrams per liter (4.2 days after induction, 8.6 day total cycle time), and 80 milligrams per liter (3.2 days after induction, 8.1 day total cycle time) during the first, second, and third cycles, respectively. The total extracellular protein and active rAAT concentration during the cyclical process are plotted in FIG. 2. Table 3 provides the summary of rAAT productivities (calculations used time points where the maximum rAAT activity was actually observed). Even though the third induction was conducted using gravity sedimentation and the cells were not drained completely dry, rAAT accumulation in the medium was as rapid as that during the first two inductions.

rAAT concentration. In the second and third expression phases, the total protein concentration and the rAAT concentration leveled off almost concurrently. During the third growth phase, after the partial medium exchange, cell viability increased while rAAT concentration decreased from 57 to 0 milligrams per liter over two days, and total protein also decreased from 300 to 70 milligrams per liter over four days. Active rAAT, as a percentage of total extracellular protein, reached maximum levels of 30%, 38%, and 20% during the first, second and third cycles, respectively.

Figure 3:
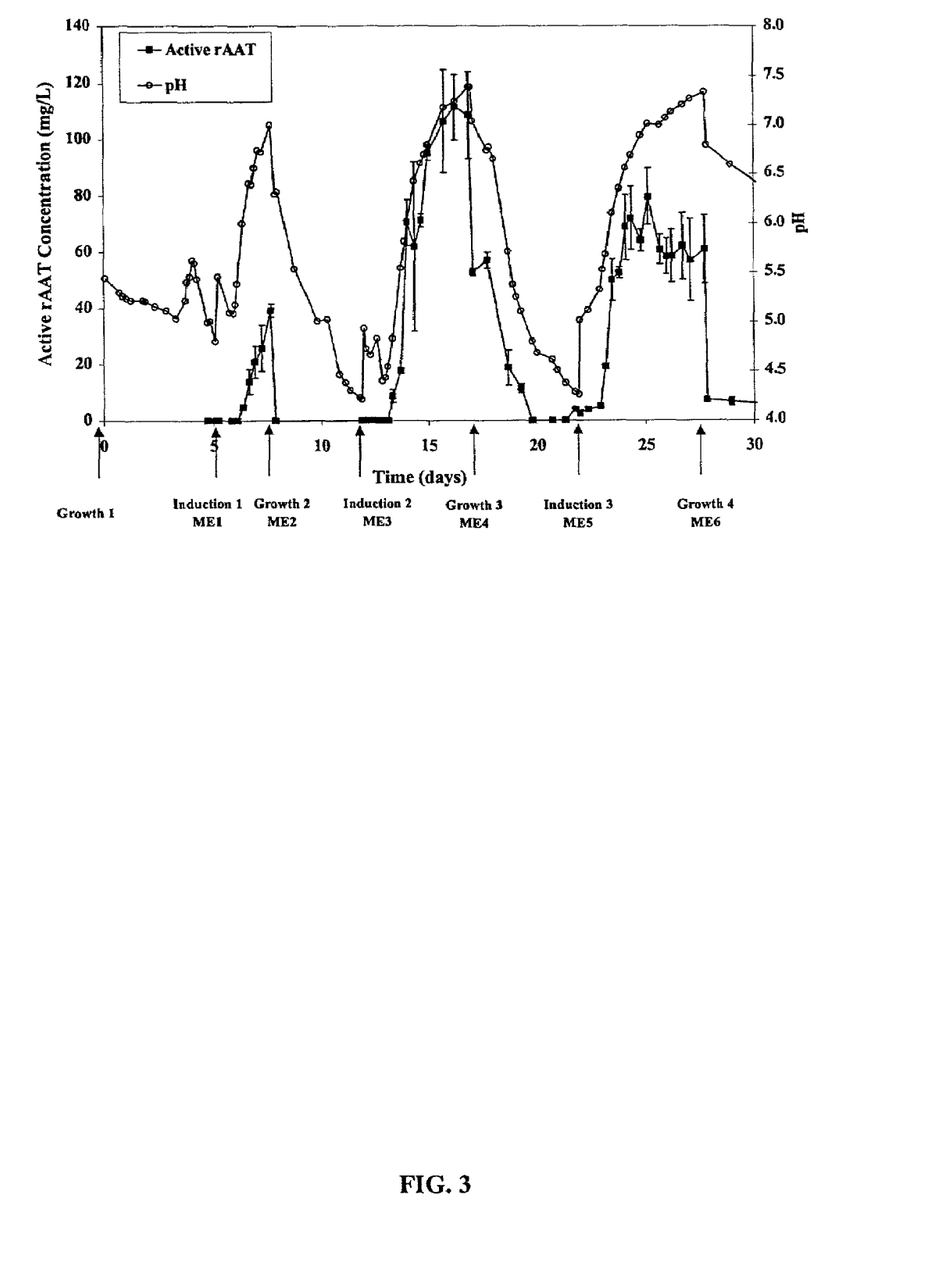
FIG. 3. Extracellular functional rAAT concentration and culture pH. Activity of rAAT was determined by measuring its inhibition of porcine pancreatic elastase. The pH of the culture was monitored continuously online. The pH of the culture was not controlled during the runs.

FIG. 3 shows the relationship between the functional rAAT concentration and pH changes during the three expression phases. The pH trend showed fairly reproducible, cyclic behavior; the pH decreased during growth phases (from pH 5.6–7.0 to 4.2–4.8) and increased sharply during the protein expression phases (from pH 4.4–5.1 to 7.0–7.4). Maximal pH levels (from pH 5.0 to pH 7.54) correlated with maximal levels of active rAAT production.

5. Characterization of rAAT Protein Produced in Transgenic Rice Cell Culture

Medium samples from growth and induction phases were analyzed by SDS-PAGE followed by immunoblotting. Samples taken after addition of AA(−) medium showed increasing levels of protein that reacted with AAT-specific antibodies, up to the time of medium exchange. Samples from AA(+) medium had little or no detectable rAAT when analyzed by immunoblots. This demonstrated that produc-

TABLE 3

Maximum Functional Recombinant Alpha-1-Antitrypsin Production

| Cycle | $t_{express}$ (days) | Active rAAT Concentration (mg/L) | Yield (mg/g dw) | Volumetric Productivity (mg/(L day)) | rAAT/Total Protein (%) |
|---|---|---|---|---|---|
| 1 | 2.5 | 40 | 12 | 4.6 | 30 |
| 2 | 4.2 | 110 | 17 | 11.4 | 38 |
| 3 | 3.2 | 80 | 9 | 6.6 | 20 |

The volumetric productivity calculation for each cycle depended on the duration of the growth phase and the time at which maximum rAAT concentration was observed during the expression phase. Using the maximum observed rAAT concentrations, the cycle duration to reach the maximum, and an approximate working volume of 4.5 liters, the volumetric productivity for each cycle was 4.6, 11.4, and 6.6 milligrams of rAAT per liter per day, respectively. The yield of rAAT per gram of dry weight (using the total biomass measured immediately after the induction medium exchange) was 12, 17, and 9 milligrams rAAT per gram of dry weight for each of the three cycles, respectively. This corresponds to specific productivities of 1.6, 2.0, and 1.1 milligrams rAAT per gram of dry weight per day.

The three cycles produced a total of 840 milligrams of functional rAAT over a 24.4 day period in a total liquid volume of eleven liters. The overall volumetric productivity over the three cycles was 7.7 milligrams rAAT per liter per day.

Figure 2:
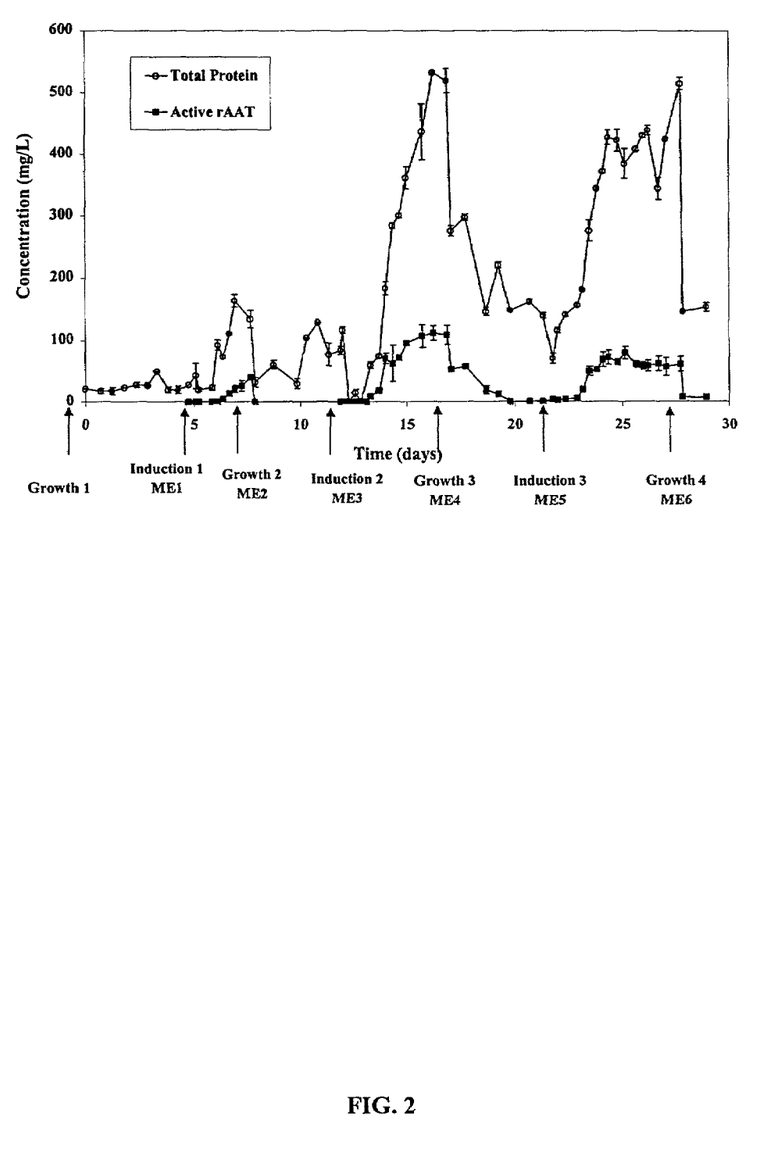
FIG. 2. Production of active rAAT during the cyclical operation. Activity of rAAT was determined by measuring its inhibition of porcine pancreatic elastase. Extracellular active rAAT and total extracellular protein concentration are shown. Total protein concentration was determined by Bradford assay.

During the three expression phases, the total extracellular protein concentration reached maximums of 160, 530, and 510 milligrams per liter, respectively (FIG. 2). Increases in total protein concentration correlated with increases in the tion of rAAT under the control of the RAmy3D promoter resulted in inducible production of the protein after removal of metabolizable sugars.

Medium samples taken during induction phases showed increasing amounts of protein recognized by AAT antibodies, as determined by Western blot analysis. The increases in immunoreactive rAAT protein correlated with increases in rAAT inhibitory activity during the induction phase.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for production of recombinant human $\alpha_1$-antitrypsin polypeptide using semi-continuous culture of transgenic rice cells comprising a heterologous expression cassette comprising a polynucleotide encoding the human $\alpha_1$-antitrypsin polypeptide, wherein said polynucleotide is operably linked to a RAmy3D promoter, the method comprising the steps of measuring the induction medium pH, and after the induction medium pH increases, exchanging the induction medium with a growth medium, and isolating the recombinant expression product from the induction medium, wherein the recombinant expression product is a heterologous protein and the induction medium pH increase correlates with a high level of heterologous protein expression.

2. The method of claim 1, wherein the human $\alpha_1$-antitrypsin polynucleotide is codon optimized for expression in rice cells.

3. The method of claim 1, further comprising measuring oxygen uptake rate of the rice cells and replacing the growth medium with the induction medium when the oxygen uptake rate is above 2.0 mmol $O_2$/Lhr.

4. The method of claim 1, comprising the step of exchanging the induction medium with a growth medium when the pH of the induction medium is above 5.5.

5. The method of claim 1, comprising the step of exchanging the induction medium with a growth medium when the pH of the induction medium is above 6.0.

* * * * *